(12) United States Patent
Lavallee et al.

(10) Patent No.: US 12,114,932 B2
(45) Date of Patent: Oct. 15, 2024

(54) METHOD AND SYSTEM FOR GUIDING POSITION AND ORIENTATION OF A ROBOTIC DEVICE HOLDING A SURGICAL TOOL

(71) Applicant: DePuy Ireland Unlimited Company, Ringaskiddy (IE)

(72) Inventors: Stéphane Lavallee, St. Martin d'Uriage (FR); Daniel Girardeau-Montaut, Gieres (FR); Claire Baegert, Gieres (FR); Nicolas Demanget, Gieres (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 1034 days.

(21) Appl. No.: 17/070,459

(22) Filed: Oct. 14, 2020

(65) Prior Publication Data

US 2021/0113270 A1     Apr. 22, 2021

(30) Foreign Application Priority Data

Oct. 16, 2019   (EP) ..................................... 19203494

(51) Int. Cl.
     *A61B 34/10*      (2016.01)
     *A61B 34/00*      (2016.01)
     *A61B 34/30*      (2016.01)

(52) U.S. Cl.
CPC .............. *A61B 34/10* (2016.02); *A61B 34/25* (2016.02); *A61B 34/30* (2016.02); *A61B 2034/104* (2016.02); *A61B 2034/107* (2016.02)

(58) Field of Classification Search
CPC .... A61B 34/30; A61B 34/10; A61B 2034/107
See application file for complete search history.

(56) References Cited

U.S. PATENT DOCUMENTS

| | | | |
|---|---|---|---|
| 2014/0276855 A1 | 9/2014 | De La Barrera et al. | |
| 2017/0189127 A1* | 7/2017 | Weir | ...................... A61B 34/20 |
| 2018/0008358 A1 | 1/2018 | Kostrzewski et al. | |
| 2018/0132946 A1* | 5/2018 | Kao | ........................ G06T 7/248 |
| 2022/0323163 A1* | 10/2022 | Bonny | ................. A61B 17/157 |

FOREIGN PATENT DOCUMENTS

| | | |
|---|---|---|
| EP | 3007636 B1 | 9/2017 |
| EP | 3443924 A1 | 2/2019 |

* cited by examiner

*Primary Examiner* — Olivia C Chang
(74) *Attorney, Agent, or Firm* — Condo Roccia Koptiw LLP (57) ABSTRACT

Methods and systems for guiding position and orientation of a robotic device holding a surgical tool are disclosed herein. For example, a method for guiding a robotic device holding a surgical tool configured for working a planned region of an anatomical structure can include detecting a presence of a distal tip of the tool in a target region on the anatomical structure, changing a visual aspect of a virtual representation of the target region when the tool tip is detected in said target region, computing a virtual goal defining a spatial range of position and orientation of the robotic device in which the tool is capable of working at least a determined part of the planned region, displaying the virtual goal and a representation of a tool base axis, and changing a visual aspect of the virtual goal when the representation of the base axis is inside the virtual goal.

20 Claims, 6 Drawing Sheets

METHOD AND SYSTEM FOR GUIDING POSITION AND ORIENTATION OF A ROBOTIC DEVICE HOLDING A SURGICAL TOOL

CROSS-REFERENCE TO RELATED APPLICATIONS

This application claims priority under 35 U.S.C. § 119 to European Application No. 19203494.0, filed Oct. 16, 2019, which is incorporated herein by reference in its entirety.

TECHNICAL FIELD

The present disclosure relates to a method and a system for guiding position and orientation of a robotic device holding a surgical tool.

TECHNICAL BACKGROUND

A robotic device holding a surgical tool configured to treat an anatomical structure of the patent is known from document WO 2014/198796.

Said device comprises:
- a base designed to be held in a user's hand,
- an end-effector for mounting a surgical tool, respectively a guide for guiding a surgical tool, said surgical tool being designed to treat a planned volume of a part of a patient's body,
- an actuation unit connected to said base and said end-effector for moving said surgical tool, respectively tool guide, with respect to the base in order to treat said planned volume.

Said device is particularly advantageous in that it is lightweight and compact.

Having a compact device is advantageous in comparison with a cumbersome large robot because it takes less space in the operating room. With a compact robotic device the working space is typically in the same order of magnitude as the volume of the anatomical structure to be treated. Having a small working space has the advantage to offer a good level of safety since in the worst case scenario the robot can move only inside a very limited range. However, having a small working space is also a drawback in comparison with large robots because it requires more efforts for the user to position the base of the robotic device at an appropriate location that will make it possible to treat the anatomical structure in one step or in a limited number of steps.

SUMMARY OF THE DISCLOSURE

It is thus desirable to define a method allowing guiding the position and orientation of a robotic device holding a surgical tool.

Some embodiments relate to a method for guiding position and orientation of a robotic device holding a surgical tool configured for working a planned region of an anatomical structure, the robotic device comprising a base and an actuation unit coupled to the base and configured to move the surgical tool relative to the base, the method comprising:
- providing a user interface displaying a virtual representation of the anatomical structure and a virtual representation of a target region on the anatomical structure;
- detecting a presence of a distal tip of the tool in the target region;
- changing a visual aspect of the virtual representation of the target region when the tool tip is detected in said target region;
- based on the position of the target region, computing a virtual goal defining a spatial range of position and orientation of the robotic device in which the tool is capable of working at least a determined part of the planned region of the anatomical structure;
- displaying the virtual goal and a virtual representation of an axis of the base on the user interface, and changing position and orientation of said virtual representation of the base axis as a user changes position and orientation of the robotic device while maintaining the tool tip in the target area;
- changing a visual aspect of the virtual goal when the virtual representation of the base axis is inside the virtual goal.

According to optional embodiments, which may be combined if technically possible:
- the method may further comprise displaying an instruction to a user to place the distal tip of the surgical tool in the target region of the anatomical structure;
- detecting the presence of the distal tip of the tool in the target region may comprise determining relative positions of the distal tip and the anatomical structure by a localization system;
- the target region may be computed based on the planned region to be treated and/or a tool path to be implemented to treat the planned region;
- the target may be computed as an ellipsoid centered on a central portion of the planned region to be treated, said ellipsoid defining a spatial range of position of the tool tip to treat the planned region;
- computing the goal may comprise determining a range of position and orientation of the base allowing the tool tip to work at least the determined part of the planned region, and determining a size and shape of the goal representative of said determined range;
- the method may further comprise setting the determined part of the planned region to be treated by the tool;
- the tool may be a burr.

Some embodiments relate to a system configured to implement the method described above.

Said system comprises:
- a localization system configured to determine relative position and orientation of the surgical tool and the anatomical structure;
- a user interface configured to display a virtual representation of the anatomical structure and a virtual representation of a target region on the anatomical structure;
- a processing unit coupled to the user interface, configured to:
  (i) based on localization data from the localization system, detect a presence of a distal tip of the tool in the target region;
  (ii) change a visual aspect of the virtual representation of the target area displayed on the user interface when the tool tip is detected in said target region;
  (iii) computing a virtual goal defining a spatial range of position and orientation of the base of the robotic device in which the tool is capable of working at least a determined part of the planned region of the anatomical structure,
- the user interface being configured to displaying said virtual goal and a virtual representation of an axis of the base of the surgical tool;

(iv) changing position and orientation of the virtual representation of the base axis displayed on the user interface as a user changes position and orientation of the robotic device while maintaining the tool tip in the target area;

(v) changing a visual aspect of the virtual goal displayed on the user interface when the virtual representation of the base axis is inside the virtual goal.

BRIEF DESCRIPTION OF THE FIGURES

Further features and advantages of the method and system will be described in the following description, based on appended drawings wherein.

DETAILED DESCRIPTION OF EMBODIMENTS

The method and system may be implemented in a surgical intervention intended to work a planned region of an anatomical structure of a patient. The surgical intervention is carried out with a robotic device holding a surgical tool adapted to work the anatomical structure.

In some embodiments, the surgical intervention may be hip or knee surgery, in particular treatment of femoroacetabular impingement (FAI), unicompartmental knee arthroplasty (UKA) and total knee arthroplasty (TKA). The anatomical structure to be treated may thus be a bone such as the pelvis, the femur and/or the tibia, and the treatment consists in removing a planned volume of the bone.

However, the method and system are not limited to these specific applications. In particular, the anatomical structure to be treated may not be a bone, and the treatment applied to said anatomical structure may not imply removing a volume of said part.

For example, the robotic device can be used for drilling, sawing, milling bones in any type of orthopaedic surgery performed to place various types of implants accurately (knee, hip, ankle, foot, wrist, shoulder, etc.), sawing and milling bones in cranio-facial surgery, reshaping teeth to fit with inlays or onlays in dentistry, drilling holes to place dental implants, inserting screws in bones for traumatology, drilling tunnels for ligament reconstruction, performing one or multiple planar or dome osteotomies of bones, removing cement during a revision procedure, placing bone fragments accurately together, drilling inside the pedicles of vertebrae, removing cartilage defects, taking healthy parts of bone or cartilage in order to graft them, inserting inlays, implants, or grafts at precise locations, placing needles accurately during interventional radiology procedures, etc.

As will be explained in further detail below, the robotic device is used in a context in which a region of the anatomical structure to be treated is planned before the surgical intervention.

Planning of the region to be treated is performed using pre-operative images (e.g. CT, MRI, Ultrasound images, 3D X-rays, PET, etc.) or intra-operative 3D data (e.g. intra-operative CT, intra-operative MRI, Ultrasound images, 2D or 3D intra-operative X-ray images, geometric data provided by localizing systems and providing 3D points, clouds of 3D points, surfaces reconstructed from clouds of 3D points, etc.)), or both.

Multiple computer-assisted surgery methods may be used to register the planned region with a coordinate system attached to the anatomical structure to be treated.

Typically, intra-operative images or data are used to register pre-operative images in a unique coordinate system attached to the anatomical structure to be treated, and usually represented by a tracker.

Figure 1:
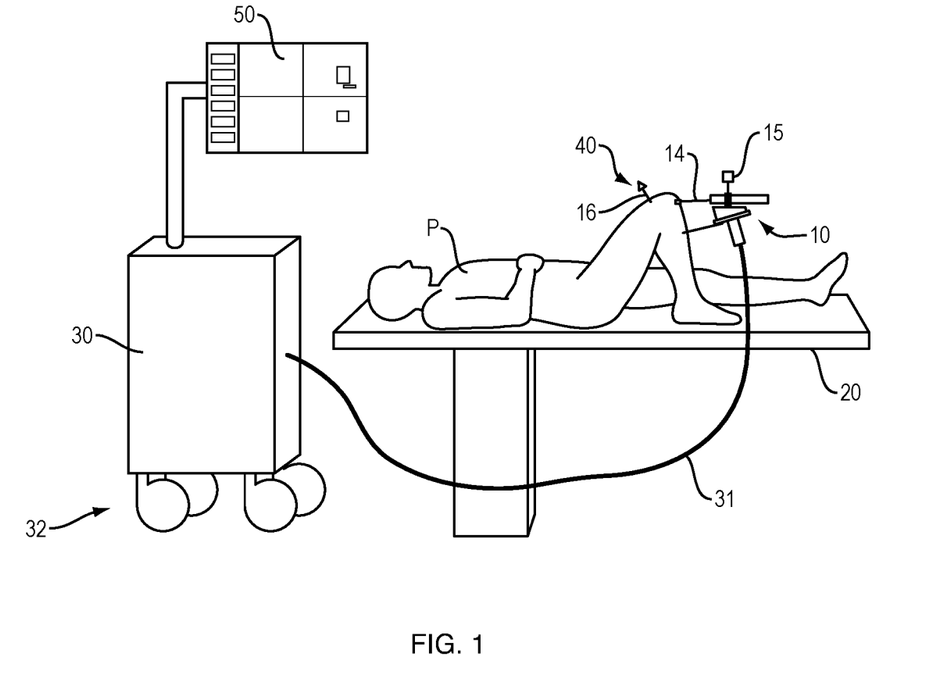
FIG. 1 is a general view of the system implemented during a surgical intervention.

Using any of these conventional computer-assisted surgery methods, the result is that the region to be treated has a known geometric representation in a coordinate system attached to the anatomical structure, and whose movements are tracked in real-time by a localization system. Various localization technologies, including optical localization and electromagnetic localization, are known and may be used in the surgical intervention FIG. 1 shows a general overview of the system.

A patient P is lying on an operating table 20, e.g. in view of unicompartmental knee arthroplasty (UKA).

To that end, a tool 14 which is intended to remove a 3D volume from the tibial and femoral bones is supported by a robotic device 10 that is manipulated by a surgeon (not shown).

The robotic device 10 is connected to a control unit 30.

Said control unit typically comprises power supply, AC/DC converters, motion controllers to power the AC/DC motors of the actuation unit, fuses, real time control system interface circuits.

The system also comprises a localization system 40, such that the pose of the robotic device, the tool and/or the bone to be treated is tracked in real-time and is shared between a real time control system and a planning system.

At least one coordinate system 16 is attached to the anatomical structure to be treated while at least one coordinate system 15 is attached to the tool and/or the robotic device.

The localization system measures the relative motions between both coordinate systems 15, 16 at high frequencies.

The data obtained by the localization system are transferred to the control unit 30 via any suitable connection, with wires or wireless (not shown here).

The real time control system is able to carry out the proposed real time control algorithms at a reasonably high frequency.

Based on the volume to be removed and the previously removed volume and the actual pose of the robotic device with respect to the bone to be treated, the real time control system calculates an optimal tool path.

There are many well-known algorithms in the robotics and machine literature for optimal milling path generation based on geometric information like binarization of the volume to be removed, or iso-parametric path generation algorithms from numerical control machining.

In FIG. 1, the connection is represented by a wire 31 but it may instead be wireless if the robotic device is battery-powered.

The control unit and localization system may be arranged in a cart 32 that can be moved in the operating room.

The system also comprises a user interface 50 that is intended to display feedback information to the surgeon and enables system configuration by the surgeon.

Said user interface 50 may advantageously comprise a screen, which may be located on the same cart 32 as the control unit and localization system.

A surgical system wherein the control unit, localization system and/or user interface are embedded in the robotic device itself would still be within the scope of the invention, provided that the embedded units are powered by a sufficiently powerful battery and that their size and weight do not hinder the manipulation of the device by the user.

Figure 2:
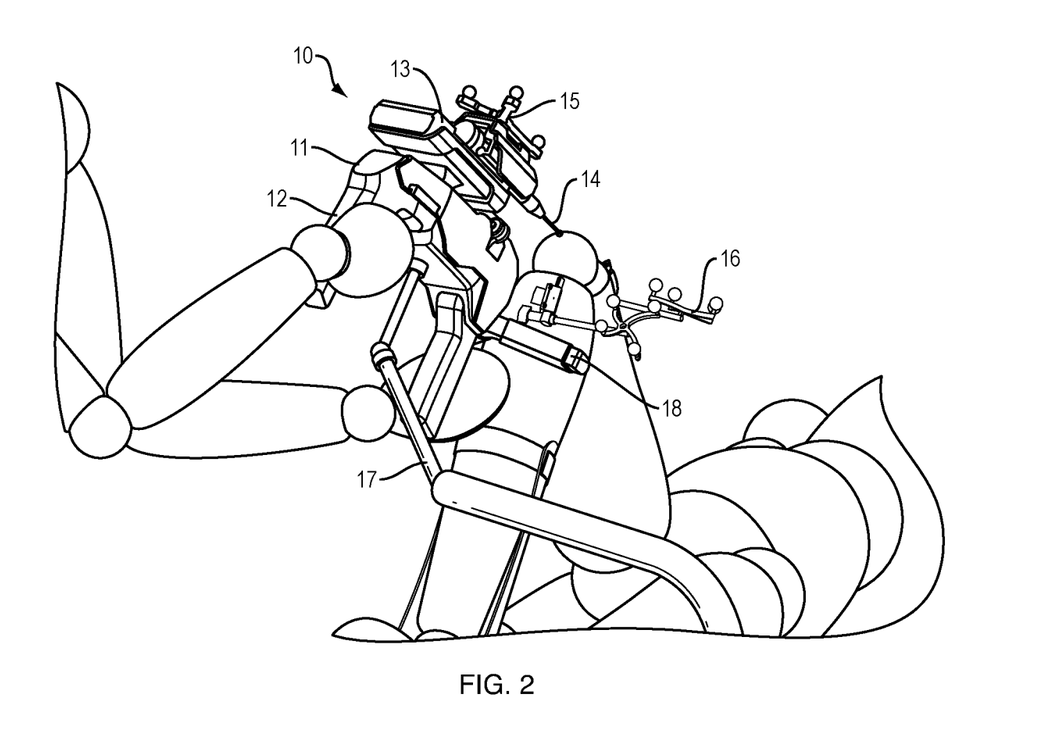
FIG. 2 is a perspective view of a robotic device holding a burr.

FIG. 2 is a perspective view of a robotic device holding a surgical tool configured for working a planned region of an anatomical structure.

The robotic device 10 comprises the following components:
- a base 11, which is configured to be handheld by the surgeon via a handle 12,
- an end-effector on which a surgical tool 14 dedicated to the intended treatment can be mounted,
- an actuation unit 13 connecting the end-effector to the base, in order to move the tool with respect to the handheld base for treating the planned volume, said actuation unit having a given number of degrees of freedom depending on the application.

Optionally, the robotic device may comprise a support unit 18 connected to the base or to the end effector and that comprises at least one element intended to make contact with the part to be treated or an area of the patient's body adjacent to the part to be treated so as to provide a partial mechanical link between the base or the end-effector and the part to be treated. Such a support unit is described in particular in document WO 2014/198784.

Optionally, in combination or not with the above-mentioned support unit, the handling of the handheld device may be assisted by a lockable holding arm 17 that supports the base of the handheld device and that is connected to a mechanical support such as the operating table.

In the illustrated embodiments, the tool is a burr comprising a spherical tip, but the disclosure is not limited to this tool. In particular, the tool may be a burr with another tip shape, such as a barrel burr, an oval burr, a cone burr, a straight side cutting burr, a tapered cross-cut fissure burr, etc. Alternatively, the toll may be a drill.

Figure 3:
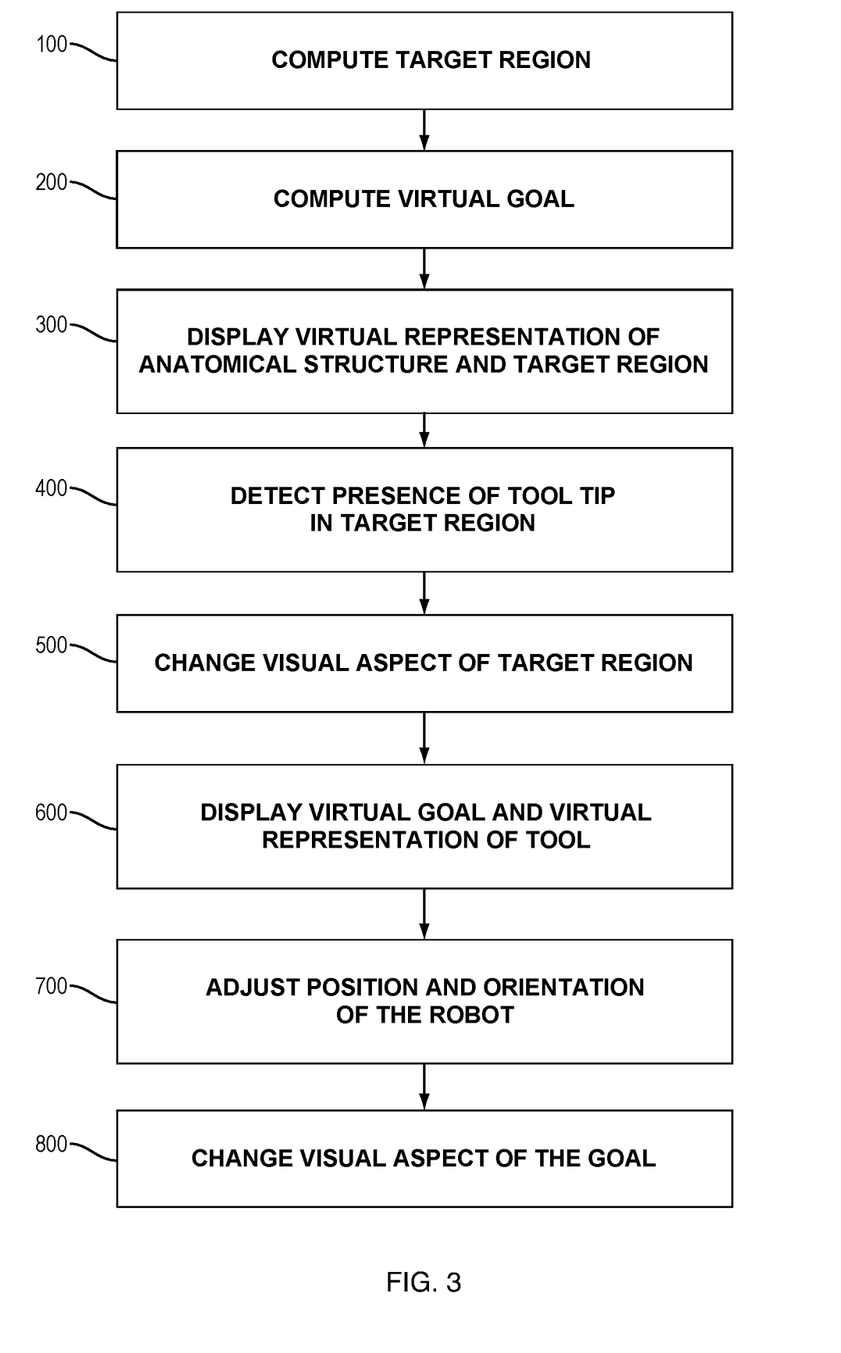
FIG. 3 is a flowchart of the method.

FIG. 3 is a flowchart of an embodiment of the method. The order of the steps presented in this flowchart is not imperative and may be changed depending on the skilled person's choices to design the method.

Before the surgical intervention, the user plans the intervention on the planning system, based on pre-operative and/or intra-operative medical images and data.

This planning step is conventional and will not be described in detail here. It is specific to each application. For example, in the case of TKA, planning of knee prosthesis on a femur requires definition of five cutting planes on the bone. In the case of FAI, planning of the volume to be removed from the femoral head and neck requires definition of a complex shape to be removed in order to retrieve a shape that has normal geometric parameters, such as the sphericity of the femoral head.

The planning system may form part of the surgical system; otherwise, the planning system may be provided separately and connected to the control unit.

During the surgical intervention, the user may either use preoperative data/images together with intra-operative registration methods, or use directly intraoperative data/images.

In both cases, the result of the planning consists of at least one continuous region to be treated by the tool, the pose of said region to be treated being determined in the coordinate system of the anatomical structure to be treated.

Based on the planned region, and possibly on technical constraints relating to the surgical treatment of the planned zone, a trajectory of the tool is computed. Various methods for computing a trajectory are known from the skilled person and will thus not be described here.

Said planned trajectory is then transferred to the control unit.

The control unit initializes its sub-systems and the robotic device is ready to use.

If the robotic device comprises a support unit, before the treatment starts, the support unit has to be connected to the anatomical structure to be treated or an adjacent body part to provide a partial mechanical link between the robotic device and the anatomical structure to be treated.

However, the method may be carried out without any support unit and in such case the user handles the robotic device in his hand with a free motion anywhere in the space surrounding the patient's body. Another possibility is that the user is assisted by the above-mentioned holding arm that supports the robotic device, the holding arm being locked in a fixed configuration once the desired position and orientation of the robotic device has been achieved.

The following method may be implemented to guide position and orientation of the robotic device.

In preliminary steps that may not belong to the method itself, the planned trajectory has been computed and transferred to the control unit.

During the guiding process, the robotic device is in a neutral position, and the tool is in a known position relative to the base of the robotic device, e.g. in a rest position, parallel to an axis of the robotic device. A relationship between the position and orientation of the base of the robotic device and the position and orientation of the tool may be determined thanks to the values of the position encoders of the robotic device and the geometric model of the robotic device, as it is commonly done in robotics.

The anatomical structure and the tool may be equipped with trackers that are tracked by the localization system. The localization system thus allows determining in real time relative positions of the anatomical structure and the tool.

In step 100, a target region is computed. The target region is a volume in which the user has to place the distal tip of the tool as an initial step of the process of determining an optimal position and orientation of the robotic device to execute the planned treatment. The target region may include not only a surface region of the anatomical structure, but also an outer volume extending from said surface region, in order to take into account possible inaccuracies in the determination of the external shape of the anatomical structure.

According to an embodiment, the target region may be computed based on the planned region to be treated and/or a tool path to be implemented to treat the planned region.

In particular, the target region may be computed as an ellipsoid centered on a central portion of the planned region to be treated, said ellipsoid defining a spatial range of position of the tool tip to treat the planned region.

In other embodiments, the target region may be computed as the two-dimensional shape of the tool tip (e.g. a circle if the tool tip is spherical).

In other embodiments, the target region may be computed as a three-dimensional envelope of the tool, with a determined margin around the tool shape, whose virtual representation may be semi-transparent.

In step 200, a virtual goal is computed based on the target region. Said virtual goal represents a spatial range of position and orientation of the robotic device allowing the tool to work at least a determined part of the planned region of the anatomical structure. Preferably, the whole planned region should be treated in a single step without requiring any repositioning or reorienting of the robotic device. However, this may not be always possible. Thus, it may be acceptable to set a threshold defining a minimal amount (e.g. 80%) of the planned region to be treated with the robotic device in the position and orientation to determine. The size and shape of the goal may depend on said determined amount.

The computation of the virtual goal may advantageously take into account tool positioning constraints. For example, the robotic device may not be placed in any position relative to the anatomical structure, but within a convenient range of position (e.g. in front of the incision providing access to the anatomical structure to be treated). Besides, presence of the tool may have to be prevented in some zones. For example, in the case of UKA, the tool should avoid the patella, the ligaments, and the opposite bone of the knee joint (e.g. if the tibia is treated first, care must be taken to the femur). The size and shape of the goal may depend on said possible conflicts.

Therefore, the goal may be computed again as soon as any anatomical structure whose position is known moves of more than a determined threshold.

Thus, the virtual goal may be computed to optimize the position of the base of the robotic device.

In some embodiments, the virtual goal may be computed at a later step of the method, before step 600.

Figure 4:
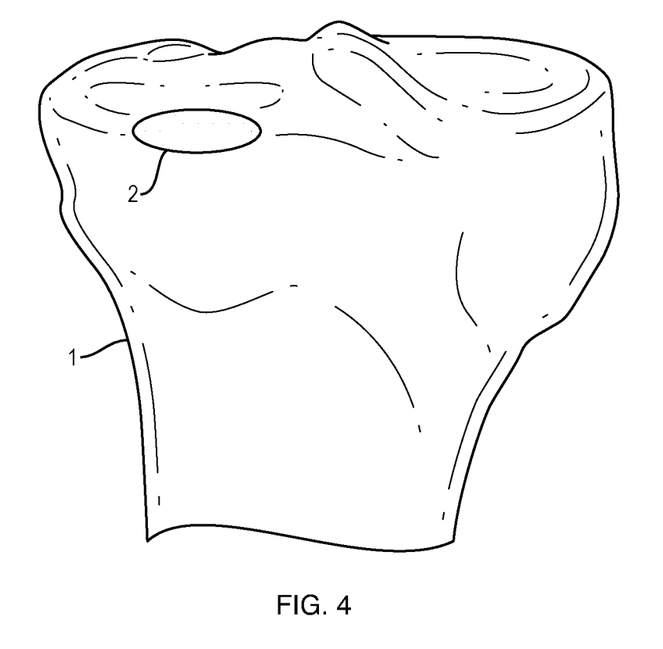
FIG. 4 represents a virtual representation of the anatomical structure to be treated and a virtual representation of a target region into which the tool tip has to be placed, as displayed by the user interface.

In step 300, a virtual representation of the target region is displayed on the user interface with a virtual representation of the anatomical structure to be treated (see FIG. 4).

In step 400, the user then has to place the distal tip of the tool in the target region, and to maintain it during the process of determining the optimal position and orientation of the robotic device.

The user interface may display an instruction to the user to do so.

It may be convenient for the user to put the tool tip in contact with the anatomical structure, the anatomical structure thus forming a support for the tool during the process. However, this is not compulsory provided that the user maintains the tool tip in the target region throughout the guiding process.

The position of the tool tip in the target region may be detected using localization data provided by the localization system.

In step 500, said detection triggers a change in the visual aspect of the virtual representation of the target region on the user interface. Said visual aspect may be a color or a texture of the target region. For example, the target region may be represented with a red color when the tool tip is not in the target region, and in green when the tool tip is in the target region.

In step 600, the virtual goal is displayed on the user interface. A virtual representation of an axis of the base may be also computed and displayed (see FIG. 5). The visual aspect (e.g. color, texture) of the virtual goal may change depending on whether the virtual base axis is inside the goal or not. For example, as long as the virtual base axis is not inside the virtual goal, the virtual goal may be represented with a red color, and with a green color when the virtual base axis is located inside the virtual goal.

It is to be noted that, in this guiding step, the base axis is the same as the tool axis, since the actuation unit is in a neutral position relative to the base. Thus, in FIG. 5, the circle represents the tool tip 3, but the shaft represents the base axis 5.

In some embodiments, the virtual goal may be displayed as early as the virtual representation of the target region, in step 300. However, the user may be confused with too much information provided at one time. Thus, it may be preferable to display the virtual representation of the target region in step 300 and of the virtual goal only after step 500.

In some embodiments, once the user has placed the tool tip in the target region, the virtual representation of said target region may disappear and the virtual goal may be displayed instead.

In step 700, the user has to move the base of the robotic device in order to find an optimal position and orientation of the robotic device. Since the tool is tracked by the localization system, its position and orientation relative to the anatomical structure may be determined in real time. The user interface thus displays in real time the displacement of the virtual tool relative to the virtual goal.

Figure 6:
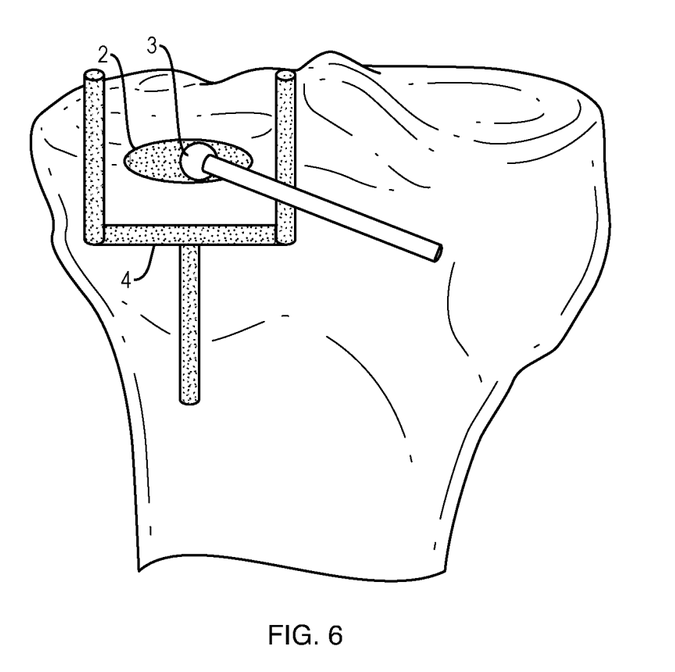
FIG. 6 represents a virtual goal and a virtual representation of the tool on the virtual representations of the anatomical structure and target region, as displayed by the user interface when the position and orientation of the robotic device allows the tool to work a determined part of the planned region of the anatomical structure.

In step 800, the visual aspect of the goal is changed when the virtual tool enters the goal (see FIG. 6).

At this stage, the user knows that, if he maintains the robotic device in the current position and orientation, the tool will be able to treat the planned region—or a set amount of said planned region.

If a holding arm is used to hold the robotic device, the holding arm may then be locked in its current position.

The robotic device may then be operated to execute the surgical plan.

During use of the robotic device, the base axis may be no longer displayed and only the representation of the tool tip, moving along the cutting trajectory, may be displayed, in order not to confuse the user with too much information.

Figure 5:
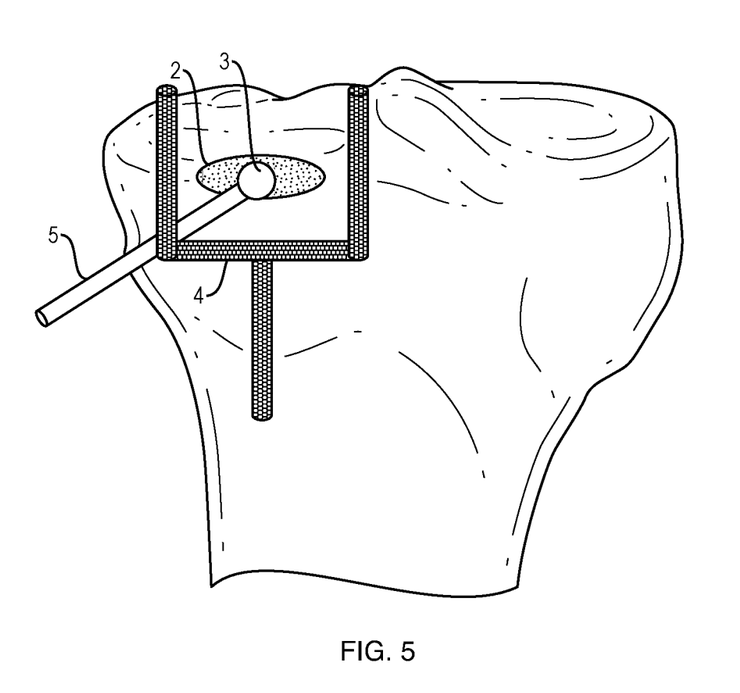
FIG. 5 represents a virtual goal and a virtual representation of the tool on the virtual representations of the anatomical structure and target region, as displayed by the user interface when the position and orientation of the robotic device does not allow the tool to work a determined part of the planned region of the anatomical structure.

Of course, the shape and visual aspect of the target region and the goal are given for illustrative purposes and may differ from the representations of FIGS. 4-6.

Figure 7A:
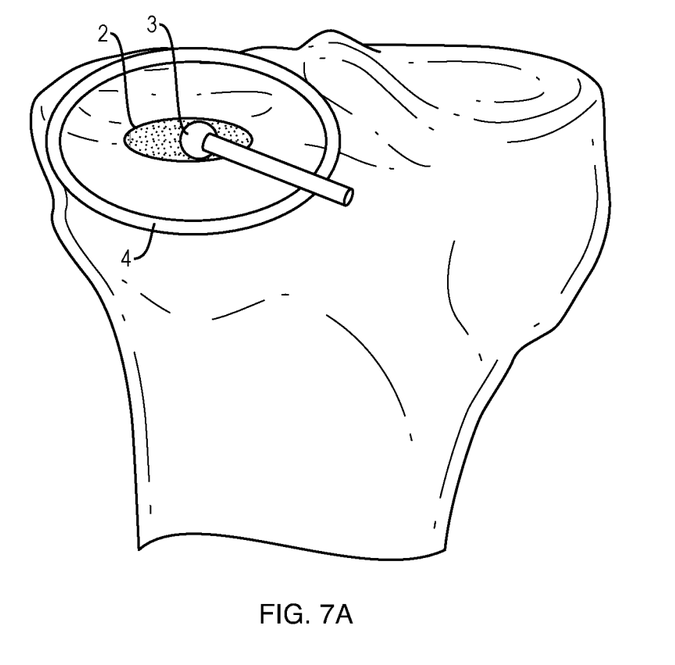
FIGS. 7A-7B show various embodiments of the virtual goal.
Figure 7B:
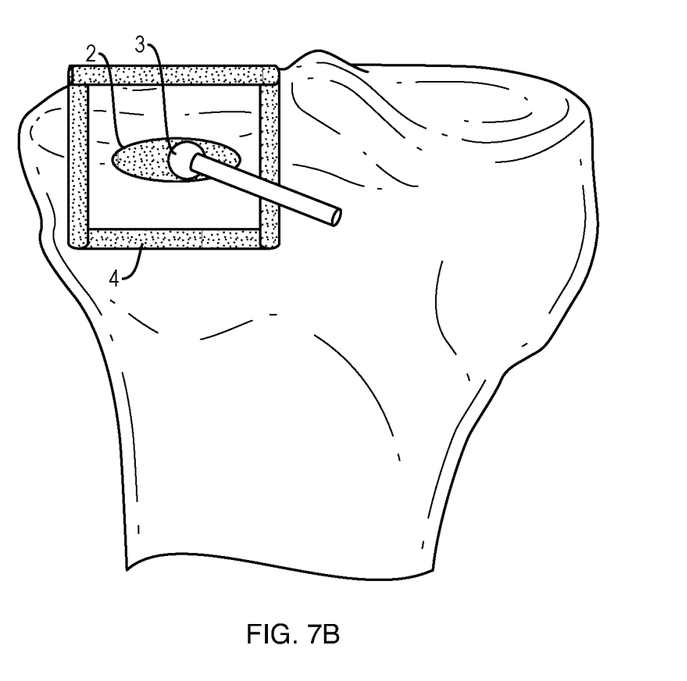

For example, while the virtual goal 4 has the shape of a football goal in FIGS. 4-6, the virtual goal may have a ring or torus shape (see FIG. 7A) or a rectangular shape (see FIG. 7B), but the skilled person may select any other suitable shape.

The above guiding process may be carried out before beginning the treatment of the planned region.

For some reasons, the treatment may be interrupted before the whole planned region has been treated.

In such case, it is possible to carry out again the guiding process to determine an optimal position and orientation of the robotic device to continue working the remainder of the planned region, but the target region and the goal may be computed to take into account the trajectory required to finalize the treatment.

REFERENCES

WO 2014/198796
WO 2014/198784

The invention claimed is:

1. A robotic surgical system, comprising:
   a robotic device comprising a base and an actuation unit coupled to the base and configured to move a surgical tool relative to the base;
   a localization system configured to determine relative position and orientation of the tool and an anatomical structure of a patient; and
   a control unit configured to:
      generate virtual representations of a target region on the anatomical structure according to a treatment plan, a base axis associated with the tool, and a goal representing a spatial range of position and orientation of the robotic device allowing a distal tip of the tool to work in the target region, wherein the virtual goal representation is not generated until after the tool tip is detected in the target region;
      change a visual aspect of the virtual target region in response to the tool tip being detected in the target region; and
      change a visual aspect of the virtual goal in response to the virtual base axis aligning inside the virtual goal as a user changes position and orientation of the robotic device while maintaining the tool tip in the target region.

2. The system of claim 1, further comprising a lockable holding arm to lock the position and orientation of the robotic device after the change in the visual aspect of the virtual goal.

3. The system of claim 1, wherein the control unit is further configured to change the visual aspect of the virtual target region by changing a color or a texture of the virtual target region and to change the visual aspect of the virtual goal by changing a color or a texture of the virtual goal.

4. A robotic surgical system, comprising:
   a robotic device comprising a base and an actuation unit coupled to the base and configured to move a surgical tool relative to the base;
   a localization system configured to determine relative position and orientation of the tool and an anatomical structure of a patient; and
   a control unit configured to:
      generate virtual representations of a target region on the anatomical structure according to a treatment plan, a base axis associated with the tool, and a goal representing a spatial range of position and orientation of the robotic device allowing a distal tip of the tool to work in the target region, wherein the virtual goal is generated only if a threshold amount of the target region can be treated;
      change a visual aspect of the virtual target region in response the tool tip being detected in the target region; and
      change a visual aspect of the virtual goal in response to the virtual base axis aligning inside the virtual goal as a user changes position and orientation of the robotic device while maintaining the tool tip in the target region.

5. The system of claim 4, wherein the control unit is further configured to cause the user interface to display the virtual goal as a user selected shape.

6. A system for guiding position and orientation of a robotic device holding a surgical tool configured for working on a planned region of an anatomical structure, the robotic device comprising a base and an actuation unit coupled to the base and configured to move the surgical tool relative to the base, the system comprising:
   a localization system configured to determine relative position and orientation of the surgical tool and the anatomical structure;
   a user interface configured to display a virtual representation of the anatomical structure and a virtual representation of a target region on the anatomical structure, wherein the target region is displayed as a shape representing a spatial range of position of a distal tip of the tool to treat the planned region; and
   a processing unit coupled to the user interface, configured to:
      based on localization data from the localization system, detect a presence of the tool tip in the target region;
      change a visual aspect of the virtual representation of the target region displayed on the user interface when the tool tip is detected in the target region;
      compute a virtual goal defining a spatial range of position and orientation of the base of the robotic device in which the tool is capable of working on at least a determined part of the planned region, wherein the user interface is configured to display the virtual goal and a virtual representation of a base axis associated with the surgical tool;
      change position and orientation of the virtual representation of the base axis displayed on the user interface as a user changes position and orientation of the robotic device while maintaining the tool tip in the target region; and
      change a visual aspect of the virtual goal displayed on the user interface when the virtual representation of the base axis is inside the virtual goal.

7. The system of claim 6, wherein the processing unit is further configured to cause the user interface to display an instruction to place the tool tip in the target region.

8. The system of claim 6, wherein the processing unit is further configured to change the visual aspect of the virtual representation of the target region by changing a color of the virtual representation of the target region.

9. The system of claim 6, wherein the processing unit is further configured to change the visual aspect of the virtual representation of the target region by changing a texture of the virtual representation of the target region.

10. The system of claim 6, wherein the processing unit is further configured to change the visual representation of the base axis based on an axis defined by the tool.

11. The system of claim 10, wherein, when the actuation unit is in a neutral position relative to the base, the axis defined by the tool is equivalent to an axis defined by the base.

12. The system of claim 6, wherein the processing unit is further configured to change the visual representation of the base axis based on an axis defined by the base.

13. The system of claim 6, wherein of the displayed target region shape is an ellipsoid.

14. The system of claim 13, wherein the ellipsoid is centered on a central portion of the planned region.

15. The system of claim 6, wherein the processing unit is further configured to compute the virtual goal to optimize the position of the base of the robotic device and/or account for tool positioning constraints.

16. The system of claim 6, wherein the processing unit is further configured to change the visual aspect of the virtual goal by changing a color of the virtual goal.

17. The system of claim 6, wherein the processing unit is further configured to change the visual aspect of the virtual goal by changing a texture of the virtual goal.

18. The system of claim 6, wherein the processing unit is further configured to cause the user interface to display the virtual goal as a shape of a football goal, a ring shape, a torus shape, or a rectangular shape.

19. The system of claim 6, wherein the processing unit is further configured to cause the user interface to display the virtual goal as a user selected shape.

20. The system of claim 6, wherein the processing unit is further configured to compute the virtual goal only if the at least a determined part of the planned region of exceeds a threshold amount.

\* \* \* \* \*